(12) United States Patent
Tankovich et al.

(10) Patent No.: US 8,932,278 B2
(45) Date of Patent: Jan. 13, 2015

(54) SKIN TREATMENT SYSTEM WITH TIME MODULATED LASER PULSES

(76) Inventors: Nikolai Tankovich, San Diego, CA (US); Alexei Lukashev, San Diego, CA (US)

( * ) Notice: Subject to any disclaimer, the term of this patent is extended or adjusted under 35 U.S.C. 154(b) by 0 days.

(21) Appl. No.: 13/199,415

(22) Filed: Aug. 29, 2011

(65) Prior Publication Data

US 2011/0313408 A1  Dec. 22, 2011

Related U.S. Application Data

(63) Continuation-in-part of application No. 12/590,075, filed on Nov. 2, 2009, now abandoned, which is a continuation-in-part of application No. 10/890,076, filed on Jul. 12, 2004, now abandoned.

(51) Int. Cl.
| | |
|---|---|
| *A61B 18/20* | (2006.01) |
| *H01S 3/113* | (2006.01) |
| *H01S 3/067* | (2006.01) |
| *H01S 3/16* | (2006.01) |
| *A61B 18/00* | (2006.01) |
| *A61B 18/22* | (2006.01) |

(52) U.S. Cl.
CPC ......... *A61B 18/203* (2013.01); *A61B 2018/208* (2013.01); *A61B 2018/2035* (2013.01); *H01S 3/1608* (2013.01); *H01S 3/113* (2013.01); *A61B 2018/00458* (2013.01); *A61B 18/20* (2013.01); *A61B 2018/00452* (2013.01); *H01S 3/0675* (2013.01); *A61B 18/22* (2013.01); *A61B 2018/00029* (2013.01)

USPC ................................. 606/9; 607/88; 607/89

(58) Field of Classification Search
CPC .................. A61B 18/203; A61B 18/00452
USPC ............................................ 606/9; 607/88, 89
See application file for complete search history.

(56) References Cited

U.S. PATENT DOCUMENTS

| | | | | |
|---|---|---|---|---|
| 6,050,990 | A * | 4/2000 | Tankovich et al. | 606/9 |
| 6,413,253 | B1 * | 7/2002 | Koop et al. | 606/27 |
| 2002/0002367 | A1 * | 1/2002 | Tankovich et al. | 606/3 |
| 2003/0004501 | A1 * | 1/2003 | Wilkens et al. | 606/9 |
| 2008/0287930 | A1 * | 11/2008 | Rapoport | 606/9 |
| 2010/0145321 | A1 * | 6/2010 | Altshuler et al. | 606/9 |

* cited by examiner

*Primary Examiner* — William Thomson
*Assistant Examiner* — Jeffrey Lipitz
(74) *Attorney, Agent, or Firm* — John R. Ross; John R. Ross, III

(57) ABSTRACT

A laser skin treatment process and system. The system includes features for producing a first laser beam of long pulse duration and a second laser beam of short pulse duration and a skin cooler for cooling the surface of a region of skin. The system is designed to utilize the first laser beam for heating a volume of skin tissue below the cooled surface region to a temperature to produce skin tissue modification but below skin tissue damage threshold. This volume of skin tissue is called a "thermal cavity". The second laser beam is divided into a plurality of separate laser beams that are directed through separate optical fibers and via separate paths through skin tissue to a single tiny volume of skin tissue within the thermal cavity to produce in that tiny volume mechanical damage. This tiny volume is called an energy droplet. Thus tiny regions of tissue are damaged while minimizing or preventing any significant damage to adjacent tissue.

11 Claims, 15 Drawing Sheets

ED
ALL LASERS
PLUS COOLING
AIR

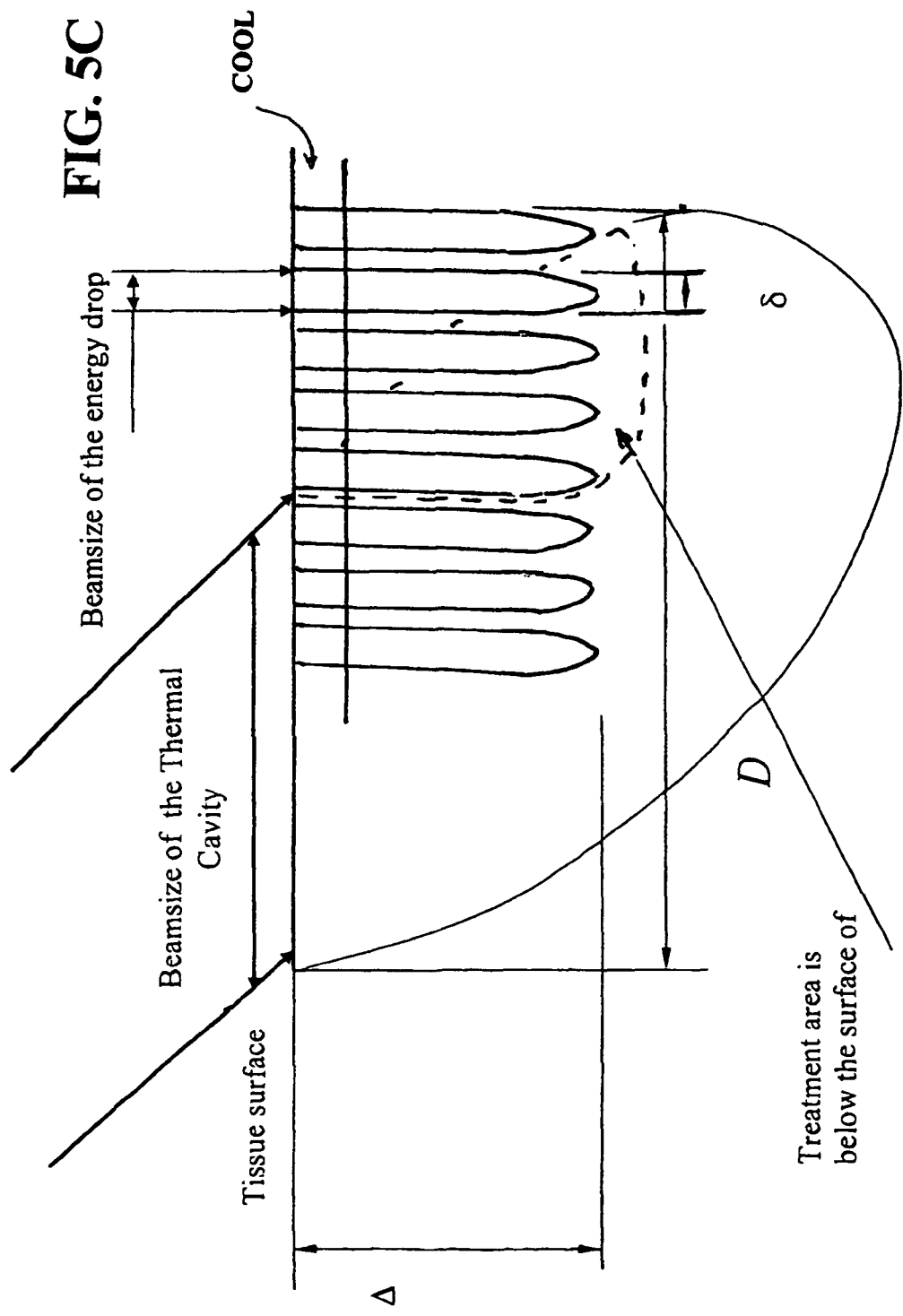

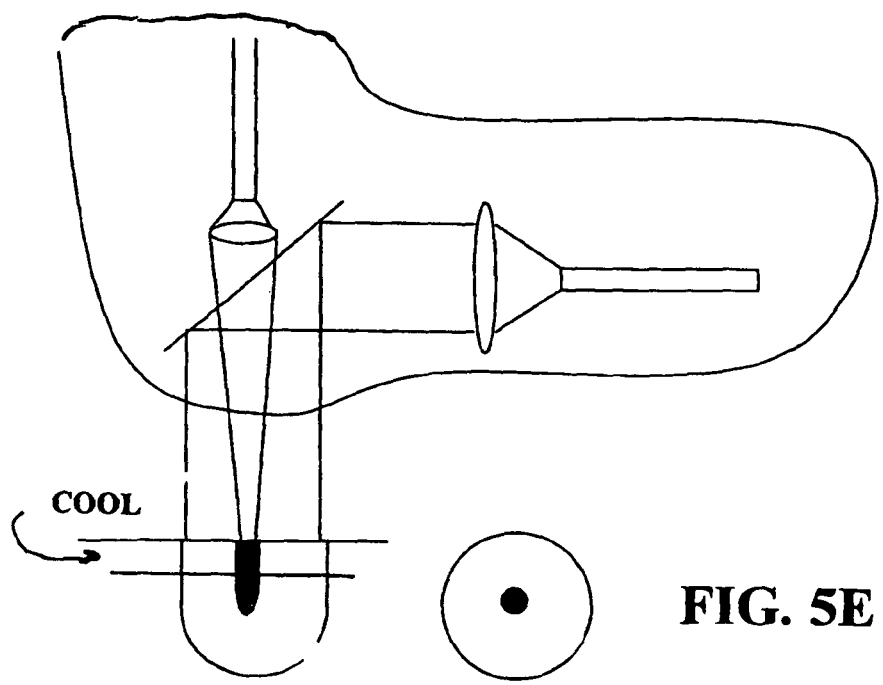
FIG. 5E
FIG. 5D
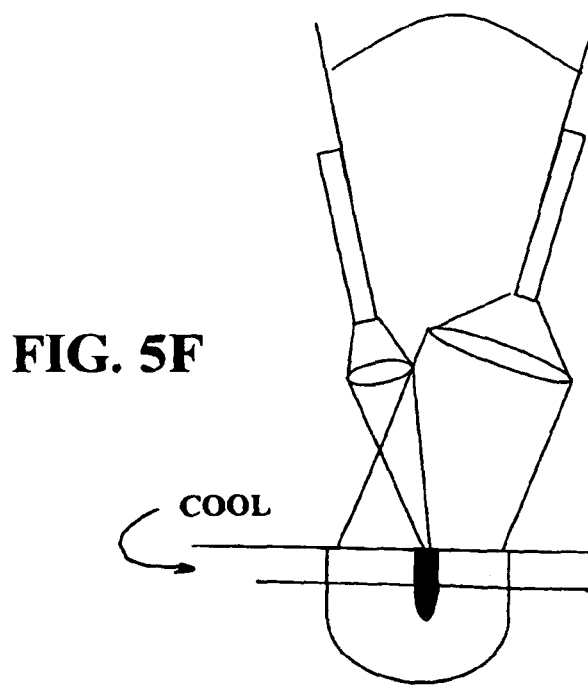
FIG. 5F
FIG. 5G

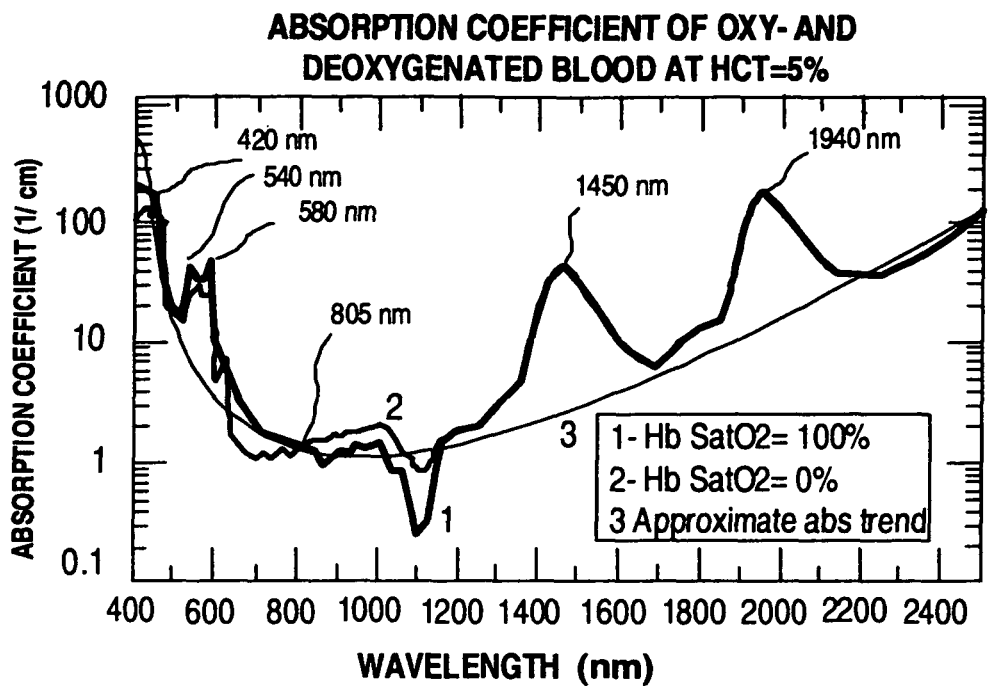
FIG. 7
FIG. 8
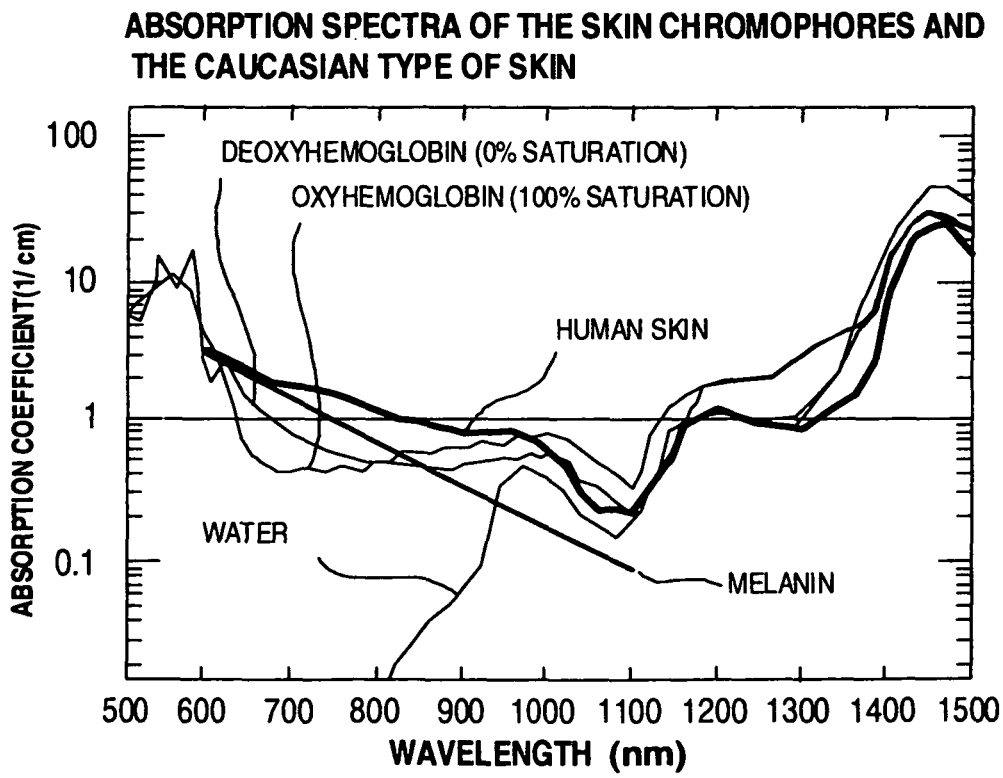

SKIN TREATMENT SYSTEM WITH TIME MODULATED LASER PULSES

CROSS REFERENCE TO RELATED APPLICATIONS

This application is a continuation-in-part of U.S. patent application Ser. No. 12/590,075 filed Nov. 2, 2009 now abandoned which is a continuation-in-part of U.S. patent application Ser. No. 10/890,076 filed Jul. 12, 2004 (abandoned) both of which are incorporated herein by reference.

FIELD OF THE INVENTION

This invention relates to fiber laser, laser diodes, and solid state laser systems and in particular to the use of those laser systems for skin treatment.

BACKGROUND OF THE INVENTION

Fiber Lasers

Fiber lasers are lasers made using optical fibers. Light emitting atoms are doped into the core of an optical fiber that partially confines the emitted light. Optical fibers with mirrors on each end can serve as laser oscillators. Optical fiber amplifiers are widely used and are similar to the fiber lasers but in the amplifiers there is no oscillation.

Laser Diodes

Laser diodes are light sources were a direct current is applied to a semiconductor and electrical energy is transformed into laser light energy—the light is monochrome, coherent with high directionality. Laser diodes typically emit in a continuous wave mode or with relative long pulses (such as hundreds microseconds). Light power could be dozens of watts from one diode. Individual diodes can be assembled together to produce more power.

Solid State Lasers

Solid state lasers use solid crystals as an active medium and a flash lamp or laser diodes as a pump source. The laser pulse duration in solid state lasers could be from a dozen femtoseconds to several seconds or continuous wave. Laser energy could be from a fraction of millijoules up to dozen of Joules.

Wavelength Selection

Some wavelengths are very preferentially absorbed in a particular type of tissue when the tissue contains a particular chromophore that has a peak or relatively high absorption at the particular wavelength. Use of a laser beam matched to a peak or relatively high absorption in tissue to treat the tissue is referred to as "selective thermolysis". Thermolysis is a chemical decomposition caused by heat. Some wavelengths are absorbed relatively uniformly in tissue and when these wavelengths are used to treat the tissue it is referred to as "non-selective thermolysis" or "homogeneous thermolysis". Choice of wavelengths is important when these lasers are used in medicine and for surgery, tattoo removal, skin peeling and hair removal. Absorption is blood is lowest in a wavelength range between about 700 nm and about 1300 nm with peaks at 1450 nm and 1940 nm as shown in FIGS. 7 and 8 and absorption in Caucasian skin is lowest in a wavelength range between about 1050 nm and about 1150 and peaks in a wavelength of about 1480 as shown in FIG. 8.

Tissue Damage

In some medical laser applications, living tissue is intentionally modified or damaged with the laser energy. Modification of tissue depends on the laser pulse duration. If the laser pulse is longer than several dozens of microseconds the typical result is temperature increases in the skin tissue caused by the energy of the laser beam being absorbed in the blood vessels, the blood in the vessels and the skin tissue. Temperature increase leads to tissue coagulation. In some cases tissue adjacent the target tissue can also be damaged. There exist, for normal skin tissue, a skin tissue damage temperature threshold. Temperatures below the threshold produce no significant damage. The threshold depends on time and temperature. For periods of time (for example, between a few milliseconds and about one second) the damage to blood and blood vessels, the damage threshold is about 44°. For shorter laser pulses, such as a few microseconds, the threshold is somewhat higher in the range of about 66° to 72° C.

If the laser pulse is very short (typically between several nanoseconds [$10^{-9}$ seconds] to and one microsecond [$10^{-6}$ seconds]) the tissue may be damaged due to explosion or evaporation in the area of laser absorption. The laser energy is absorbed by skin tissue, however laser pulse duration is very short and there is not enough time for the tissue to expand or for the heat to spread out of the laser spot. In these conditions the tissue is mechanically ruptured in the region of laser absorption.

Thermal vs. Ablation and Disruption

FIG. 9 is a chart showing the types of laser tissue interactions as a function of power density and exposure time. For pulse durations longer than about 1 microsecond the laser-tissue interactions are thermal. For pulses shorter than 1 microsecond the effects tend to be mechanical in the form of ablation or tissue disruption.

The Need

What is needed in a low cost laser system to produce precise damage in small regions of tissue while preventing of controlling damage to the adjacent tissue.

SUMMARY OF THE INVENTION

Thermal Cavities and Energy Droplets

The present invention provides a laser system and process for skin treatment. The system includes (1) components for producing a first continuous or long pulse laser beam, (2) components for producing a second very short pulse laser beam and (3) a skin cooler for cooling the surface of a region of skin. The system is designed to utilize the first laser beam for heating a volume of skin tissue below a cooled surface region to a temperature high enough for tissue modification but below skin tissue damage threshold. This volume of skin tissue is referred to herein as a "thermal cavity". The second laser beam has a much shorter pulse duration (applied simultaneously or with some delay) producing precise mechanical tissue damage. In preferred embodiments the second laser beam is divided into a plurality of separate laser beams that are directed through separate optical fibers and via separate paths through skin tissue to a single tiny volume of skin tissue within the thermal cavity to produce in that tiny volume tissue damage. The energy deposited in this tiny volume is referred to herein as an energy droplet. Thus, tiny regions of tissue are mechanically damaged via ablation or disruption while minimizing or preventing any significant damage to adjacent tissue.

The system also includes a laser hand piece designed to deliver skin surface cooling so as to create the thermal cavity below the skin surface without over heating the skin in the surface region. In preferred embodiments the surface cooling is provided with a flow of cold air and the number of laser beams from the second laser is six laser beams. The cold air in preferred embodiments is at a temperature of about 0 to 3° C. and may be provided with a commercial off-the-shelf cooling air unit or with a simpler unit consisting of a blower unit, an accumulator and a tube coiled in an ice water bath. The two laser beams can be provided by a single laser system as described in the parent patent application or the two beams may be provided by two separate off-the-shelf laser units.

The Thermal Cavity

In the preferred embodiment the thermal cavity is produced by the 0° to 3° cooling air and a single laser beam from a YAP:Nd laser adapted to produce 0.3 J laser pulses, at a wavelength of 1079 nm, with a burst duration of 900 microseconds at 6 Hz repetition rate. Optical components are provided to produce a beam diameter on a skin surface of about 4 millimeters. The combination of the cooling air and the YAP:Nd laser beam produces a thermal cavity at a relatively uniform temperature of about 42° C. in a region of the skin about 4 mm in diameter and 1.5 mm to 4 mm below the skin surface. The temperature at the surface is less than 36 C (which is normal body temperature). The thermal cavity responds relatively uniformly for at least about six seconds. (For the thermal cavity other laser sources could be used; however, preferred sources should have relatively long pulse duration or the laser should be a continuous wave laser and the wavelength should be chosen for low skin and blood absorption.)

Energy Droplets

In preferred embodiments the energy droplets are produced by a single erbium-doped fiber laser system. This laser system is a master oscillator power amplifier fiber laser system, referred to as a MOPA fiber laser system. The laser system operates at a wavelength of 1560 nm with pulse durations of 0.2 microseconds. At this wavelength absorption in the skin and blood is relatively high. In this preferred embodiment the output of this second laser system is divided into six separate optical fibers with each fiber carrying approximately 200 nanosecond, 35 mJ pulses. All of the six beams are directed through optical fibers, lenses and prisms to a single small roughly spherical about 0.48 mm diameter damage region of the skin within the thermal cavity and centered about 0.5 mm below the skin surface.

These extremely short pulses produce skin damage in this tiny volume of skin tissue. Pulse energies are chosen to deposit between about 15 mJ and 138 mJ in a 0.055 milligram region of skin. Pulse energies are chosen to produce skin damage through photodisruption and photoablation with minimal or no thermal damage. Applicants estimate a pressure increase in this small region of about 60 atmospheres. Tissue separated by more than 0.06 millimeter from the 0.48 millimeter damage zone is heated to no more than 44° C. (111.2° F.) for less than one microsecond. The temperature then drops to about 36°. As a result there is no significant tissue damage at distances greater than 0.06 millimeter from the 0.48 millimeter damage region.

Other laser sources could be used for the energy droplets. Preferably the sources should have extremely short pulse lengths, preferably 200 nanoseconds or less and the beam should be divided into a plurality of beams (at least two) and directed at desired locations for creation of the energy droplets. Preferably the thermal cavity is created at least a few microseconds before the energy droplets are created.

BRIEF DESCRIPTION OF THE DRAWINGS

FIGS. 5A through 5I show alternative techniques for creating energy droplets below the skin surface within an thermal cavity.

FIG. 7 is a graph showing absorption coefficients in blood.

FIG. 8 is a graph showing absorption in skin.

DETAILED DESCRIPTION OF PREFERRED EMBODIMENTS

Preferred Embodiments

Figure 1:
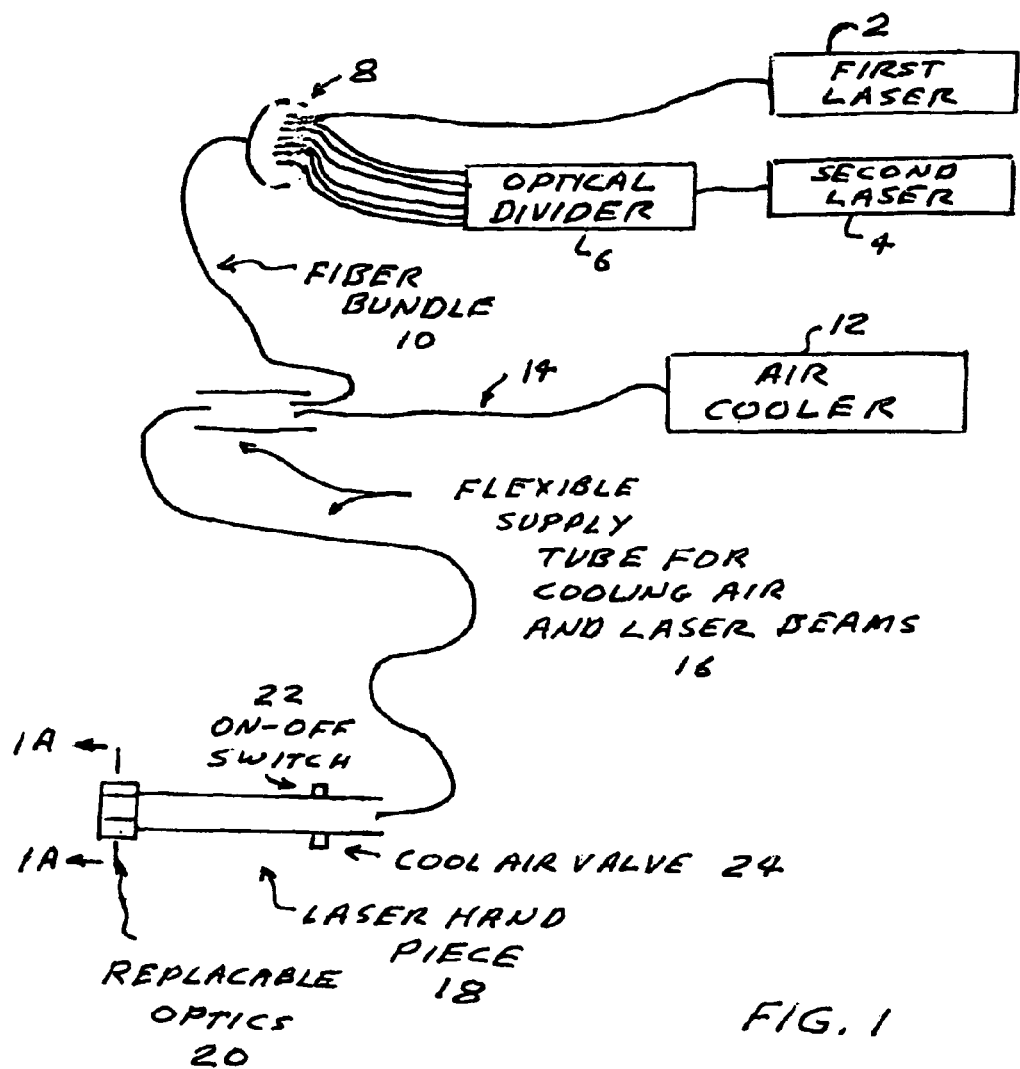
FIG. 1 is a drawing of a preferred embodiment of the present invention.
Figure 1A:
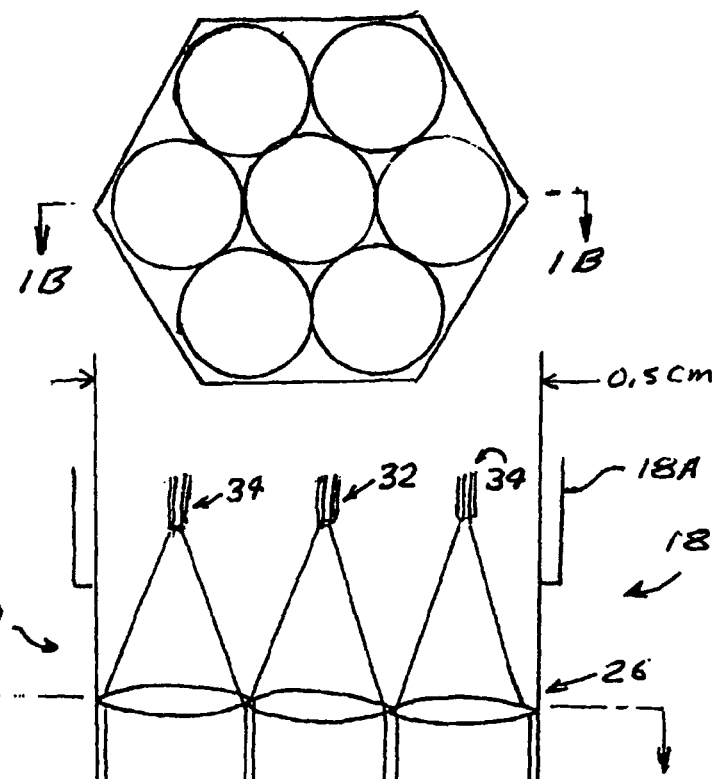
FIGS. 1A, 1B and 1C show features of laser hand piece of the preferred embodiment.
Figure 2A:
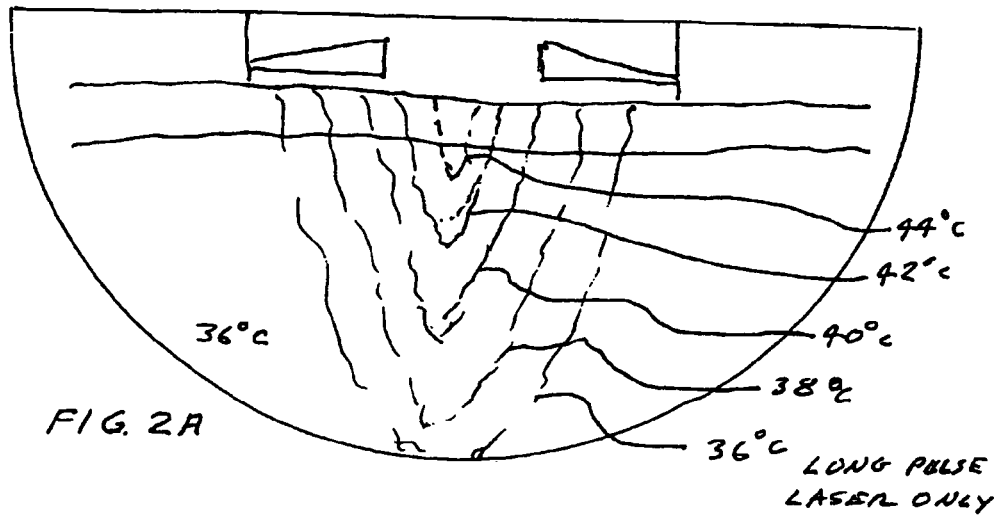
FIGS. 2A through 2E show approximate temperature contours produced by the laser beams and the cooling air.
Figure 2B:
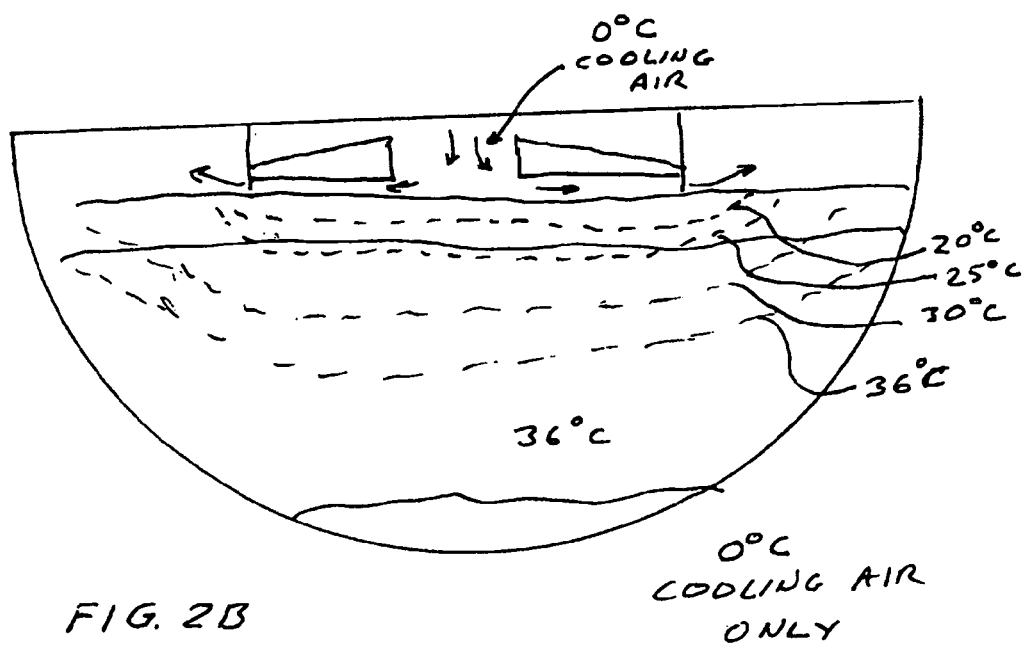
Figure 2C:
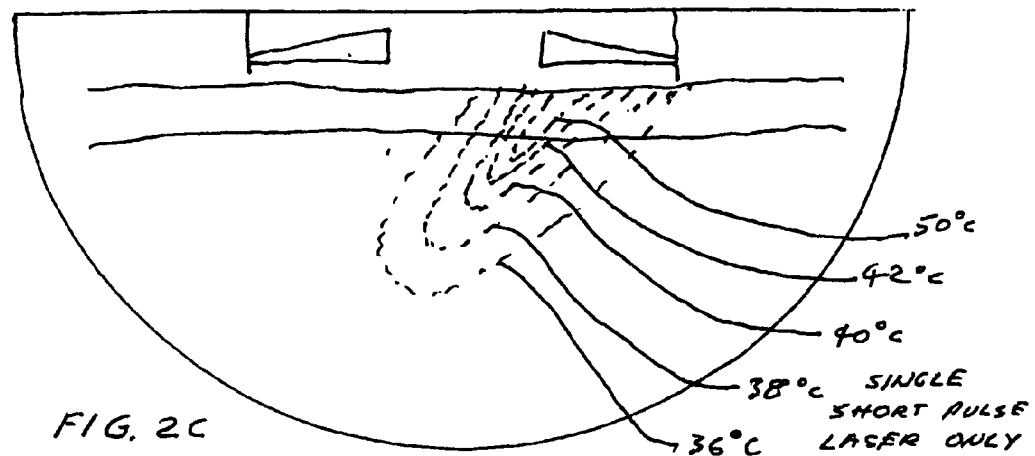
Figure 2D:
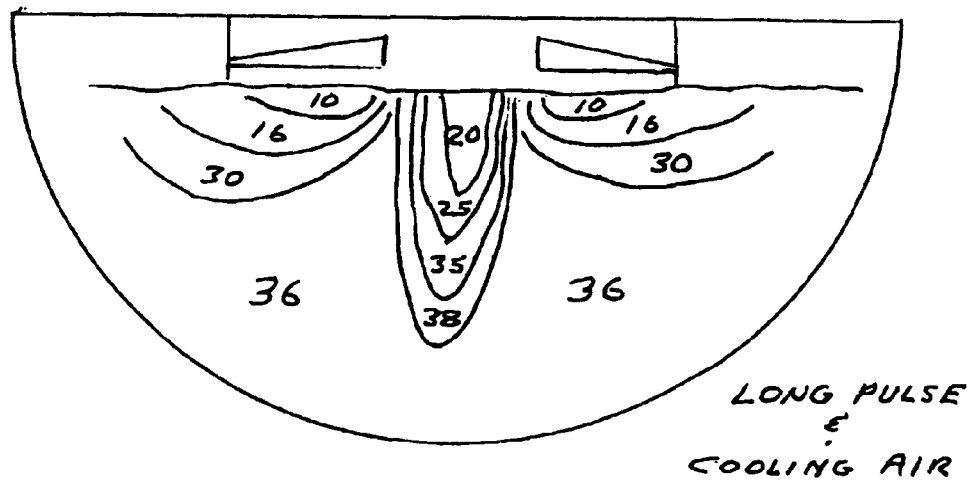
Figure 2E:
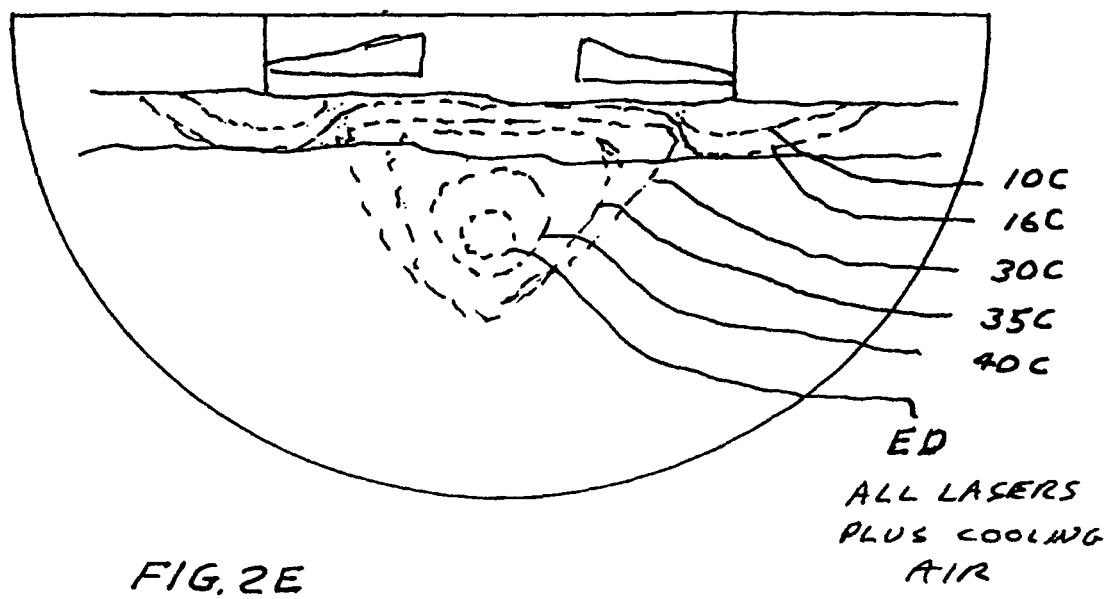
Figure 3:
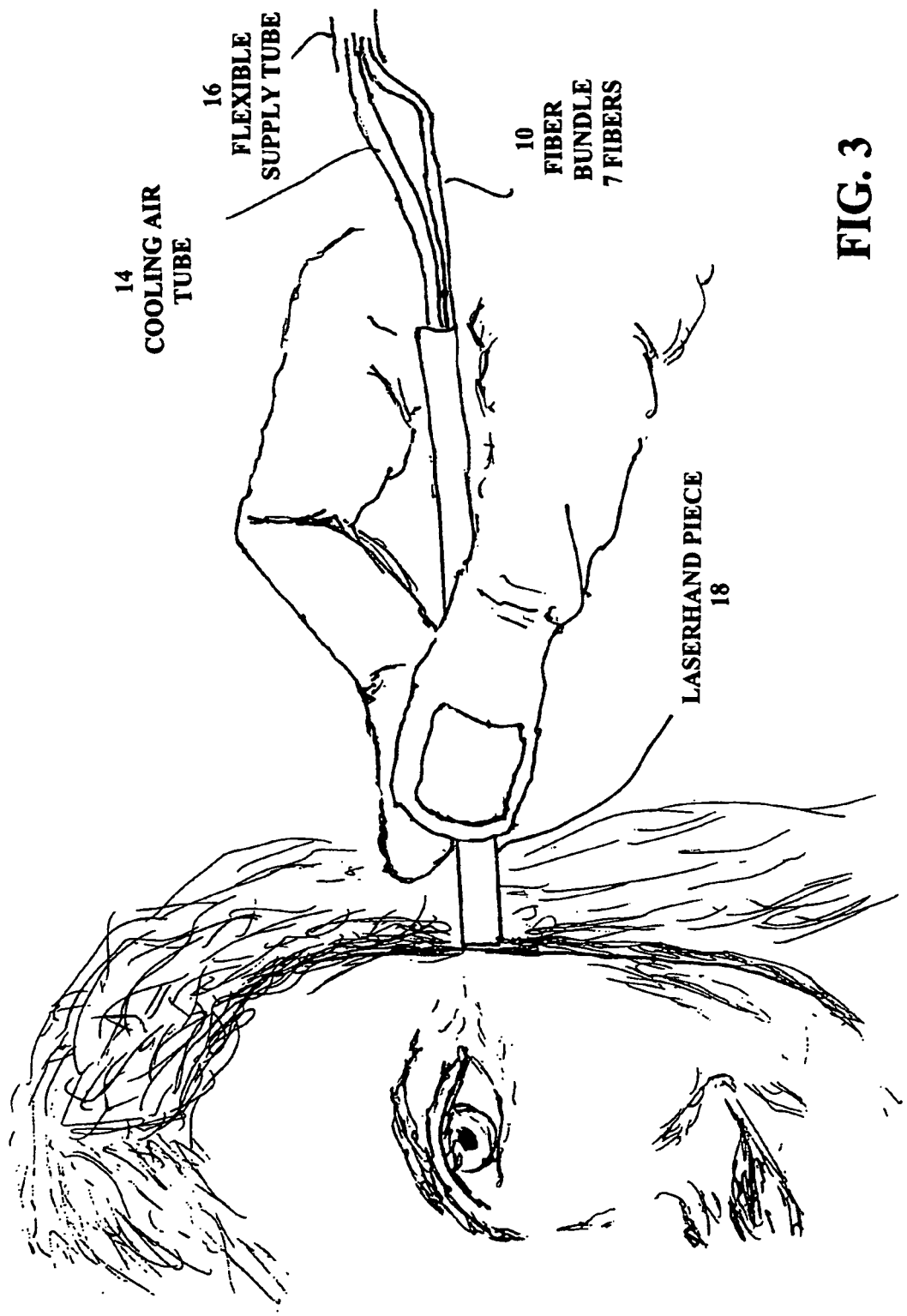
FIG. 3 shows the hand piece being applied to a patient.

FIGS. 1 through 3 show features of preferred embodiments of the present invention. As shown in FIG. 1 the embodiment includes first laser source 2, second laser source 4, an optical divider 6 for dividing the output of the second laser source into six laser beams each of the six beams are directed into separate optical fibers which fibers are combined in combiner 18 with a single fiber carrying the output of the first laser source 2. The seven fibers are transported in a fiber bundle 10 which is combined cooling air tube 14 carrying approximately zero degrees centigrade cooling air which is cooled air cooler 12. Flexible supply tube 16 carries the seven laser beams and the cooling air to laser hand piece 18 which includes a cooling air valve 24 and a laser on-off switch 22. The laser hand piece 18 includes a replaceable optics unit 20. Details of replaceable optics unit are shown in FIGS. 1A and 1B.

Figure 1B:
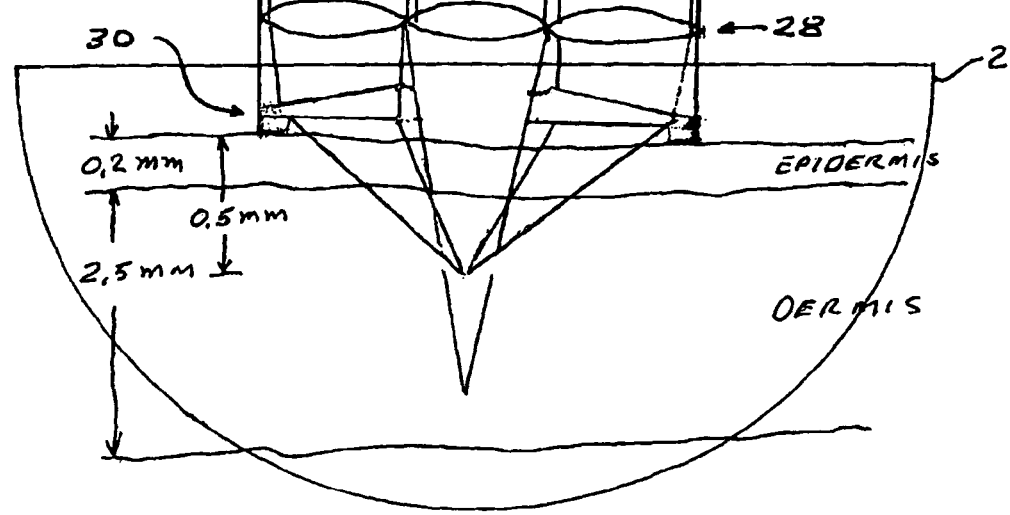
Figure 1C:
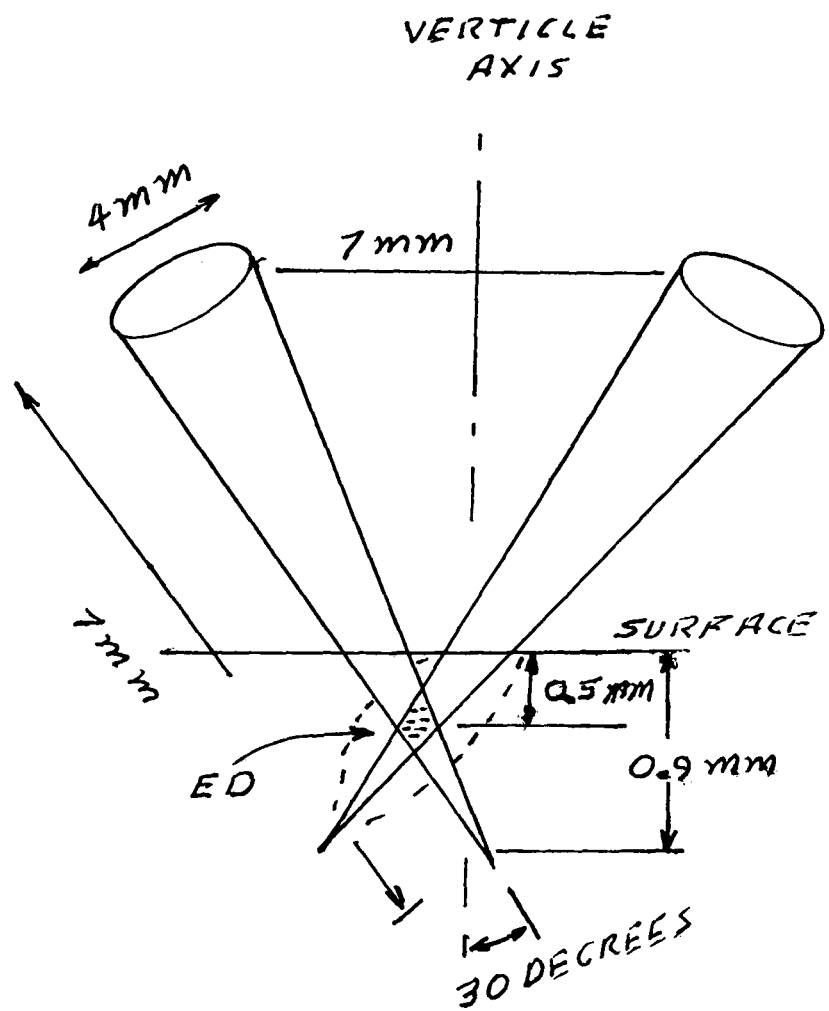

The replaceable optics unit 20 fits in the body 18A if laser hand piece 18 as shown in FIG. 1B. The optics unit includes two lens arrays of seven lenses each for focusing each of the laser beams at desired locations below the skin surface. A prism array of six prisms 28 directs each of the six beams transported in fibers 34 from the second laser to a single location about 0.5 mm below the surface of the skin where each of the beams are focused with the optical combinations of the two lenses and the prism controlling each of the six beams. The beam transported in fiber 32 from the first laser is controlled only by two lenses and is focused at a focal point about 1.0 mm below the skin surface. The reader should note that the beam traces shown in FIG. 1B are approximate traces assuming that the beam were transported in air. Since the beams are instead passing through skin tissue the actual shapes of the beams are substantially different. The general directions of the beams are correctly represented in FIG. 1C. However, the beams will be scattered in the tissue and therefore spread substantially as compared to the solid line traces in FIG. 1C as indicated by the dashed lines. Also the beams will undergo substantial absorption on the way to their focal location. Applicants have conducted computer modeling to determine the approximate actual shapes of the beams in the skin tissue.

As the photons in the beams are scattered and absorbed in the skin tissue the beam energy is converted into heat increasing the temperature of the skin tissue. The cooling air from air cooler 12 and tube 14 passes out of the center of replaceable optic unit 20 and flows along the surface of the skin as indicated in FIG. 2B and in the process cools the surface of the skin directly below optics unit 20. Based on Applicants' computer analysis Applicants have estimated temperature contour lines separately resulting from each of the seven laser beams and the cooling air. These contour lines are shown in FIG. 2A for the thermal cavity beam from the first laser; FIG. 2B for the cooling air; FIG. 2C for each of the six energy droplet beams from the second laser. FIG. 2D shows the contour lines for the combination of the beam from the first laser and the cooling air. This drawing defines the "thermal cavity". FIG. 2E shows the contour lines for all seven lasers and the cooling air. The circle labeled "ED" in FIG. 2E defines the "energy droplet" and represents photoablation or photodisruption produced by this preferred embodiment.

In the preferred embodiment the energy droplet is formed by six crossing beams within the thermal cavity. The thermal cavity is formed by the 1079 nm wavelength of the YAP:Nd (Perovskite) laser. The energy droplets are formed by the 1560 nm laser beam of the fiber laser. Using a lens with f=7 mm and diameter of 4 mm each individual beam is focused with the beam tilted to the vertical axis at 30 degrees. The crossing point of those six beams is about 1 mm above the focus point of the thermal cavity beam. The hand piece with those six beams is pre-aligned in the air. For application on skin the hand piece is placed at a distance about 5 mm from the surface of the skin. In this case the crossing point is about 0.5 mm beneath the surface of the skin. The energy droplet is roughly spherical with a diameter of about 0.48 millimeters (radius of 0.24 mm). The volume of the energy droplet is about 0.06 cubic millimeters. In this configuration the laser beam spot size on skin of each of the six beams is about 0.6 mm. The output of the second laser 4 shown in FIG. 1 is adjusted to provide a quantity of energy delivered to the energy droplet by each of the individual beams is between about 2.5 mJ and 23 mJ, so the total energy delivered to the energy droplet region by the six beams is between about 15 mJ and about 138 mJ. This amount of heat energy from the six beams is sufficient to increase temperature in the 0.06 cubic millimeter energy droplet volume (corresponding to about 0.055 milligrams of skin tissue) vaporize some to all the tiny volume producing mechanical damage but very little or no thermal damage outside the energy droplet. The specific heat of skin is about the same as for water (about 4.2 J/gram° C.), so about 15 mJ is required to increase the temperature in the energy droplet from about 35° C. to about 100° C. The latent heat of vaporization of skin tissue is also about the same as water (about 2,250 J/gram), so about 123 mJ (in excess of the 15 mJ required to heat the tissue to 100° C.) would be required to vaporize all of the 0.055 milligrams of tissue at the spot of the energy droplet.

In preferred embodiment Applicants recommend that the invention be practiced to provide photoablation or photodisruption with no significant thermal damage to the skin tissue. A good target energy level for a 0.055 milligram energy droplet would be about 30 mJ. This has the effect of keeping the damaged tissue region small and isolated from undamaged from undamaged tissue. Therefore, efforts should be made to operate in the lower range of 15 mJ to 138 mJ for a 0.055 milligram size energy droplet. For procedures designed for smaller or larger energy droplets then the deposited energy needs to be adjusted accordingly.

To deposit 30 mJ in the energy droplet with the six-fiber design shown in FIG. 1, each of the six fibers would carry sufficient energy to deposit 5 mJ in the energy droplet. For the FIG. 1 design, only about 1/7 of energy transmitted by the six beams is deposited in the energy droplet. The rest on the energy illuminating the skin surface is reflected or absorbed in tissue outside the droplet. Therefore the system should be adjusted so that each fiber would illuminate the skin surface with about 35 mJ with the beam directed at the energy droplet region.

Heat Dissipation in Thermal Cavity and Energy Droplets

The amount and the rate of energy absorption in light-absorbing chromophores depend on the laser pulse energy and duration of the pulse. The shorter the pulse duration, the higher the temperature rise in the light-absorbing medium. If the pulse duration is short enough then at the end of the pulse the absorbed energy is confined well inside the light absorbing chromophore. Alternatively, much of the heat may be dissipated into the surrounding medium if the pulse duration is very long. As an approximation, the thermal energy dissipation distance in a given period of time can be written as:

$$x = \sqrt{4\chi\tau} \quad (1)$$

where x in cm—is the thermal energy dissipation distance; $\tau$ (in seconds) is the duration of thermal energy dissipation; $\chi$ (in cm$^2$/sec) is the thermal diffusivity, which is determined by the mathematic expression $\chi = K/\rho c$ (in which K is in J cm$^{-1}$s$^{-1 \circ}$ C.$^{-1}$) is an energy absorption coefficient; $\rho$ (in g/cm$^3$) is the density of the tissue and c (in Jg$^{-1 \circ}$ C.$^{-1}$) represent the specific heat. Table 1 lists the thermal energy dissipation distances in skin during a period of 100 ns (Q-switched Yb$^{+3}$ and Nd doped fiber laser pulse duration), 100 µs (typical duration of non-Q-switched or free running Nd:YAG/YAP lasers), and 100 ms for long pulse YAP:Nd laser.

TABLE 1

The thermal energy dissipation distance x (µm) skin during period $\tau$

| $\tau$ | Dissipation Distance 10$^{-6}$ m |
|---|---|
| 10 ns | 0.03 |
| 100 µs | 3.23 |
| 100 ms | 102 |

The thermal diffusivities (cm$^2$s$^{-1}$) used in the calculation for skin is 0.001.

In addition to the thermal energy dissipation described above the absorbed laser energy can also dissipate mechanically in forms of thermal expansion of the light absorbing chromophores or generation of shock waves. The time needed for this expansion to happen is defined by:

$$t_m = x/a_s \quad (2)$$

where x is a smallest geometrical size of light absorbing chromophore, and $a_s$ speed of sound. If the laser pulse duration is shorter then $t_m$ the case of mechanical (or acoustical) confinement is taken place. In this case the absorbed energy stays within geometrical size of the light absorbing chromofore without mechanical dissipation during the laser pulse. This leads to very high pressure build up during laser pulse which then dissipates in a form of a shock wave. The shock wave can produce rupture of the tissue which contains light absorbing chromophore.

In other terms, for each laser pulse duration $\tau$ mechanical energy dissipation distance can be defined $x=a_s \tau$. Table 2 shows examples of mechanical dissipation distance for different pulse duration.

TABLE 2

The mechanical energy dissipation distance x (μm) skin during period τ

| τ | Dissipation Distance ($10^{-6}$ m) |
|---|---|
| 10 ns | 10 |
| 1 μs | 1,000 |
| 100 μs | 100,000 |

It is clear when comparing data from Table 1 and Table 2 that mechanical dissipation occurs much faster compare to the thermal energy dissipation. Neglecting the energy loss due to dissipation, the instantaneous temperature rise in a light absorbing medium at the end of a 10 ns laser illumination can be expressed as $$\Delta T = \alpha_a \phi / \rho c \quad (3)$$

where $\alpha_a$ in $cm^{-1}$ is the absorption coefficient; and $\phi$ in $J/cm^2$ is the laser fluence.

Penetration of radiation into a scattering medium (skin can be considered as a good example of a scattering medium) is defined by the absorption of the radiation in this medium and by its scattering properties. The penetration depth d is expressed by the following formula:

$$d = 1/(3\alpha_a(\alpha_a + \alpha_s'))^{1/2} \quad (4)$$

where and $\alpha_a$ is an absorption coefficient and $\alpha_s$ is scattering extinction.

Geometrical dimension of beam size D of a thermal cavity preferably should be larger or equal penetration depth defined by (4). The equations (1) and (2) define critical temporal relationship between dimensions of a thermal cavity and pulse duration of radiation that forms it.

According to the equation (1) pulse duration $\tau$ is to satisfy the relationship:

$$D > d > \sqrt{4\chi\tau} \text{ or } \tau < d^2/4\chi < D^2/4\chi$$

Droplets of electromagnetic energy are to satisfy the following relationship:

$$\Delta < D,$$

where $\Delta$ penetration depth of droplets which is in turn depends on the wavelength of the radiation, $\delta < d$, $\delta$ is a diameter of the droplets. According to this relationship pulse duration of droplets should preferably be shorter compare to pulse duration of the pulse forming the thermal cavity. Thus, the thermal cavity and energy droplets can be formed by two (or more) types of radiation with different absorption in the medium or by the same radiation with different pulse duration or by a combination of both or by beam configuration. Then, following equation (3) and the definition of the thermal cavity, the energy density and/or temperature in the droplets of energy is greater compare to the energy density and/or temperature in the thermal cavity giving a sense of using term 'droplets' to describe such a specific distribution of energy in tissue. If the pulse duration of a 'droplet' laser pulse is shorter than 1 μs then an additional mechanical confinement takes place and the energy droplet also exist in the time domain for very short time and results in high pressure pulse (shock wave).

The efficiency of conversion of light energy into the mechanical one (shock wave) is defined by $$\Delta P = \Gamma \alpha_a \phi \quad (5)$$

Where $\alpha_a$, $\phi$ are absorption coefficient and energy fluence defined above (formula (3)) and $\Gamma$ is the Gruneisen parameter $\Gamma = M\beta/\rho C_p$, where M [Pa]—is the bulk modulus, $\beta$—is the volume thermal expansion coefficient [$K^{-1}$], $\rho$—is the density [$g/cm^3$], Cp—heat capacity at constant pressure [J/kg]. For a temperature T=35 C, $\Gamma$=0.18 for water and aqueous solutions.

Figure 6:
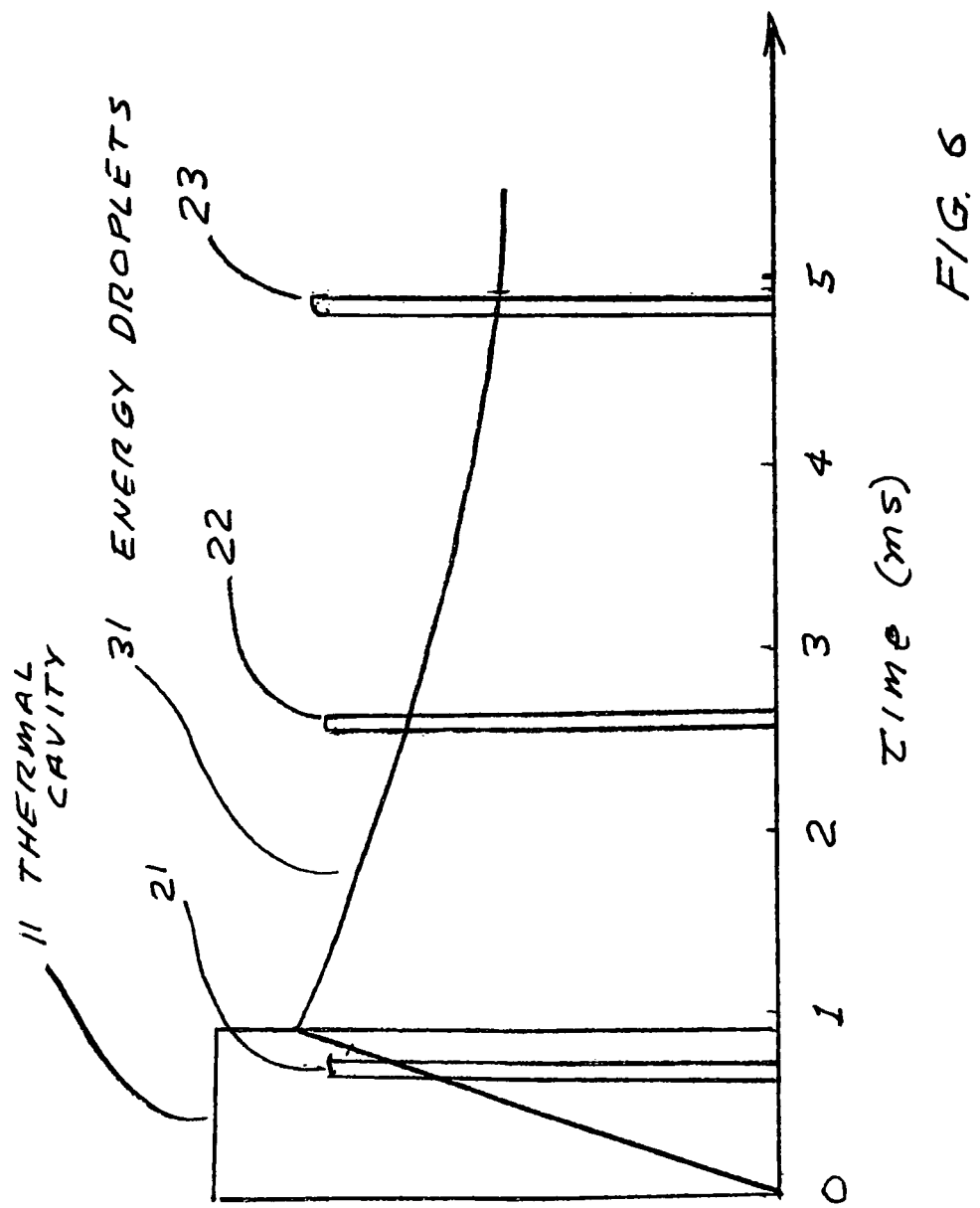
FIG. 6 Temporal shape and relative temporal position of the first laser beam (thermal cavity) and the second laser beam (energy drop).
Figure 9:
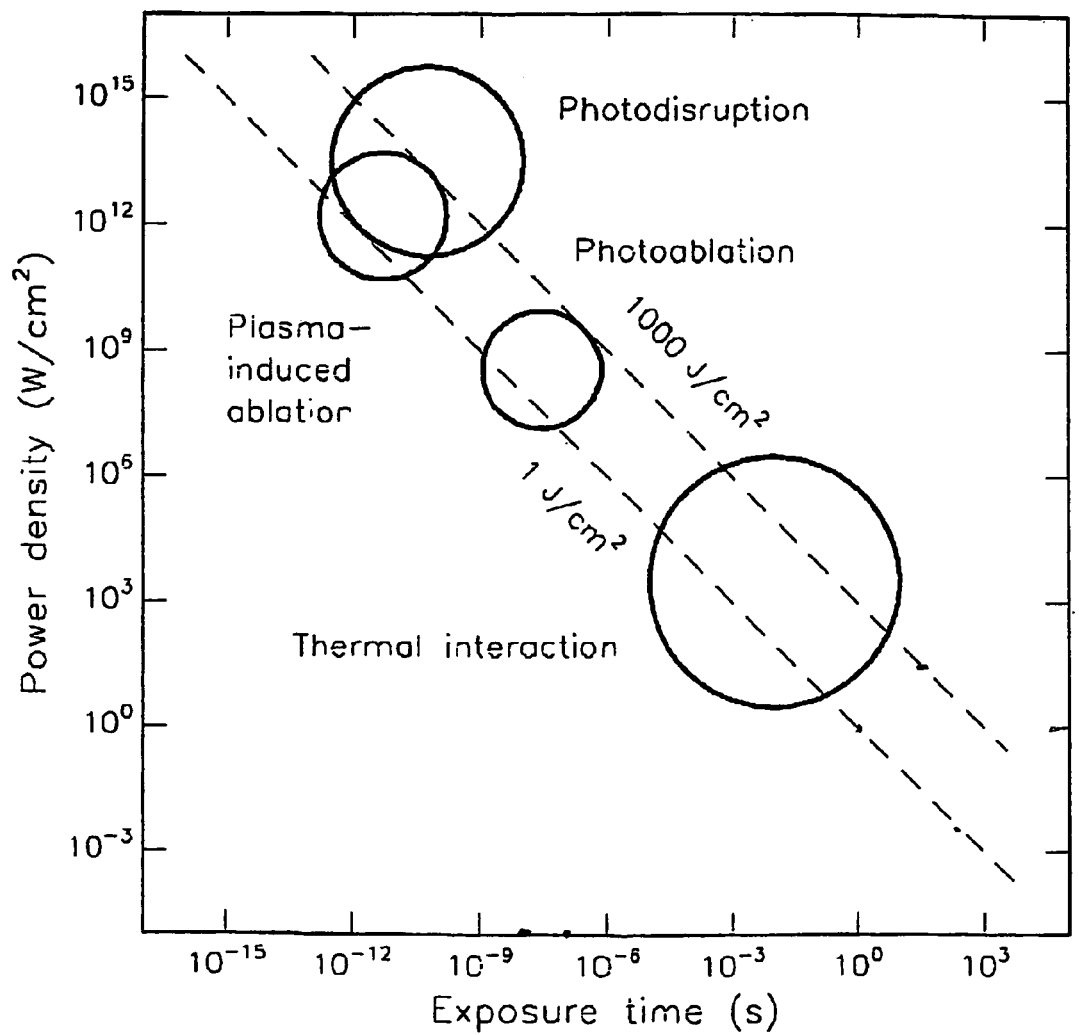
FIG. 9 is a map of laser-tissue interactions.

Thermal energy dissipation takes place much slower compare to mechanical energy dissipation. Thus it is possible to produce a thermal cavity by the first laser beam with long pulse duration and the energy droplet with mechanical confinement by the second laser beam with short laser pulse duration during or after the first laser beam. An example of such sequence of pulses is shown at the FIG. 6. In this example the thermal cavity is produced by λ=1079 nm laser beam of 900 microsecond pulse duration, the laser spot size is 4 mm and it is assume 1% expansion of the thermal cavity due to thermal dissipation. The second laser beam of λ=1560 nm of the fiber laser and pulse duration 0.2 microsecond could be applied during the first laser beam (21, FIG. 6) or up to 4 ms delay (23). For the second laser beam of a fiber laser at the fluence 3 $J/cm^2$, the pressure of the mechanically confined energy droplet could be up to 60 atmospheres.

Such specific distribution of energy is essential to a number of medical and aesthetic applications of lasers and other sources of radiation. Radiation that forms the thermal cavity does not damage the tissue, but increase overall energy deposition close to the damage threshold. In this case energy droplets provide more accurate energy delivery which is just needed for specific therapeutic effects due to supra threshold effects and spatial modulation of those effects across thermal cavity area. In specific embodiments energy droplets can be formed fixed as multi-beams crossing in the thermal cavity as shown at the FIG. 1A or they can be form via other techniques such as those indicated in FIGS. 5A through 5I.

Hand Piece

FIG. 3 shows the system in operation with the hand piece being used to treat the face of a patient. This embodiment damages tiny volumes of skin tissue about 0.5 mm below the surface of the skin. There is no significant damage to the skin surface or to any other portions of the skin outside the energy droplet. The damaged skin tissue will cause an immune response in a form of release of cytokines and stem cell factors which will create stem cell action producing new skin tissue resulting in younger looking skin. Since the skin is not damaged at the surface scaring or other surface effects are extremely unlikely.

Laser System from Parent Application

Figure 4:
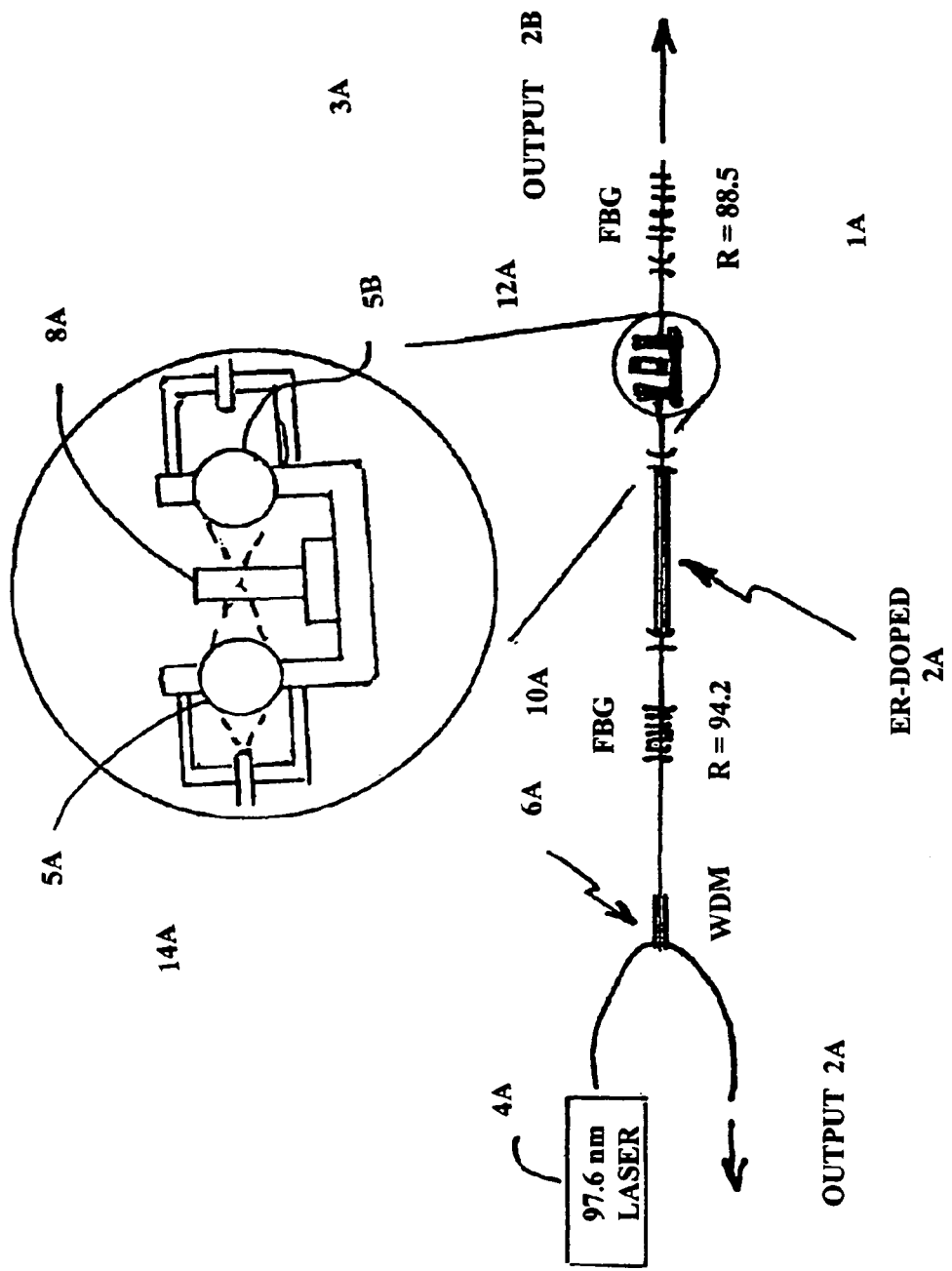
FIG. 4 is a drawing from the parent application of a laser system useful for producing two separate laser beams.

FIG. 4 is an optical schematic of Q-switched erbium laser described in detail in the parent patent application which is useful in an embodiment of the present invention. A laser cavity 1A is created with single mode erbium doped optical fiber 2A with a core diameter of 6.0 μm and a fiber length of anywhere between 0.2 m and 20 m. Applicant's preferred length is about 1 meter. The doping concentration of erbium ions is sufficient to produce about 1 dB/m to 350 dB/m absorption of the pump wavelength. Radiation from a pump diode laser 4A at a wavelength of 976 nm is launched with a wave divider multiplexer (WDM) coupler 6A into the master cavity. A $Co^{2+}$:ZnSe crystal 8A with initial transmittance $T_{in}$=70-98% and a thickness 0.3 mm-1 mm is positioned within the cavity and the cavity is defined by two fiber Bragg grating mirrors 10A and 12A with maximum reflection of 94.2% (100-95%) and 88.5% (70-98%), respectively, both gratings are designed for a wavelength of 1560 nm. The laser includes a U-bench unit 14A with a $Co^{2+}$:ZnSe crystal inside as shown in FIG. 4.

U-bench 14A is a holder having a "U" shape as shown in FIG. 4, which is placed in between two ends of fiber tips and holds those fiber ends. The fiber ends are polished at a small angle of about 9 degrees to the optical axis to exclude back reflection. A small ball type lens 5A with a focal length of about 2 mm is placed at about a double focus distance from the fiber tip as shown in FIG. 4. The lens relays the image of the fiber tip to the center of U-bench. Then the image of the first fiber tip is relayed back onto the tip of the fiber positioned on the opposite side of U-bench 14A by a second ball type lens 5B. The beam waist is about 15 μm. All surfaces of optical elements including the $Co^{2+}$:ZnSe crystal are coated to decrease reflection in the range of 1400-1800 nm. The system is aligned during fabrication. The inserted loss by introduction of a U-bench in to the fiber could be as low as 0.1 dB. In this preferred embodiment, the power density is adjusted so that the intra-cavity radiation level at the center of U-bench (i.e., the center of the $Co^{2+}$:ZnSe) is about 1 kW/cm². Other parameters of $Co^{2+}$:ZnSe crystal are:

1) absorption cross-section $\sigma_s$=5.3×10$^{-19}$ cm²;
2) upper level lifetime $\tau_s$=0.29×10$^{-3}$ s;
3) bleaching power for $Co^{2+}$:ZnSe, as low as 0.8 kW/cm².

The dependences of pulse energy (and, consequently, average power) of the laser can be estimated using the following formula for output energy of the laser operating in the passive Q switch mode:

$$E_{out} = -\frac{h\nu S_a}{4\sigma_a \gamma} \ln \frac{1}{R_1} \ln \frac{n_a^{min}}{n_a^{max}},$$

where $E_{out}$ is addressed to one of the laser outputs closed by the mirror $M_1$; $n_a^{min}$ and $n_a^{max}$ are the extremum inversion populations in AM; and hv is the energy of a laser output photon. Additional factor "2" in the denominator is introduced for accounting the Gaussian distribution of the beam in the laser cavity. The pulse energy of the pump laser is approximately constant so that pump energy is roughly proportional to pump rate. A minimum of giant pulse duration and maxima of the pulses' energy and peak power are observed close to the middle point of the passive Q switch mode. This fact allows one to manipulate with the output parameters of the laser by simply changing the pump rate.

The laser threshold was measured to be 19.3 mW at wavelength 1559.5 nm, where the laser operates in the superluminescence regime. Just above the threshold of oscillation, with pump power increased up to 20.5 mW, the laser transited to the passive Q switched regime, where stable giant pulses are generated. Rather long pulse width of the giant pulses is the result of a considerably long length of the cavity. Thus, the pulse duration can be controlled to an extent by choosing the length of the cavity. Or the laser may be designed to provide maximum total pumping of the fiber to produce maximum pulse power. Pulse duration could also be shortened using a high-doped erbium fiber of short length (less than 2 m) as an active medium of the laser. In this case pulse duration could be in the range 0.2 μs-3 μs. The repetition rate of the pulses in a train increases with the pump repetition rate up to about 50 kHz.

A $Cr^{2+}$:ZnSe crystal for Q-switch could be substituted for $Co^{2+}$:Zn. The parameters of the U-bench were chosen to produce power density of the intra-cavity radiation in the center of U-bench at about 60 kW/cm². The crystal $Cr^{2+}$:ZnSe was placed near the center of U-bench to provide location of the beam waist of 1 μm close to the crystal center. The $Cr^{2+}$:ZnSe crystal had antireflection coating at wavelength 1400-1800 nm. A sample of $Cr^{2+}$:ZnSe crystal with initial transmittance $T_{in}$=50-98% and thickness 0.3-1 mm, and the two fiber Bragg grating (FBG) mirrors with maximum of reflection of 100-95% and 70-98%, respectively. The bleaching power of a $Cr^{2+}$:ZnSe is 60 kW/cm². Using this passive Q-switch modulator pulse duration as short as 10 ns to 500 ns might be obtained depending on the pump rate and the length of the fiber laser.

Thus, by changing pump rate, concentration of erbium doping in the fiber, length of laser resonator (fiber) and a type of passive Q-switcher it is possible to vary pulse duration of the fiber laser in the range from 10 ns to 15 μs.

Other Alternatives

A preferred wavelength of YAP:Nd laser is 1079 nm, energy fluence 20 J/cm² and pulse duration 900 microsecond. In this preferred embodiment individual fiber laser operates at the output energy level 15 mJ each, individual pulse duration 0.2 μs. Both YAP:Nd and fiber laser are synchronized to deliver laser pulses approximately at the same time. Mismatch of synchronization or delay between pulses should be less than thermal relaxation time defined in formula (1), and in this case this time equals less than 4 ms (see FIG. 6). The Perovskite laser for this preferred embodiment is available at Fotona Lasers, Ljubljana, Slovenia and the fiber laser is available from IPG Photonics at Waltham, Mass.

Battery operated hand held systems are available for producing thermal cavity with energy droplets for skin rejuvenation. In those systems energy is provided by powerful laser diodes and they are available from Intenzity with office in Vancouver, BC, Canada. In this preferred embodiments laser diodes at about 980 nm maximum emission band is used to produce thermal cavity and several diodes (e.g. 1 to 4) with maximum emission around 1290 nm are used to produce energy drops. Those laser diodes at 980 and 1290 nm could be combined in one pack. The electrical power for those diodes is provided by batteries with 3V voltage rating and a control circuit. The power current needed for diode operation is about 2-3 A. This level of current is provided by current alkaline or Li-ion (lithium) type AA batteries and even re-chargeable NiMeH (nickel metal hydrate) batteries. Thus, a combination of laser diodes, batteries, control circuit and lens focusing system forms a compact hand-held system.

Powerful laser diodes in wavelength range 1290 nm are available from Covega Corporation Jessup, Md., powerful laser diodes at 980 nm are available from Spectra Physics, Mountain View, Calif.; Coherent, Santa Clara, Calif. Alkaline or re-chargeable NiMeH batteries are available from Energizer or other off-the-shelf suppliers.

Other Optics Units

In preferred embodiments each system is provided with a set of optics units 20 each providing for the energy droplet at a different location below the skin surface. Preferably, the locations will cover a range below the surface between about 0.2 mm to about 1.0 mm. The number of laser beams carrying the energy of the second laser source could be as few as two to as many as ten. The energy of the first laser source could also be divided into a number of separate fibers.

Other Beam Patterns

Figure 5A:
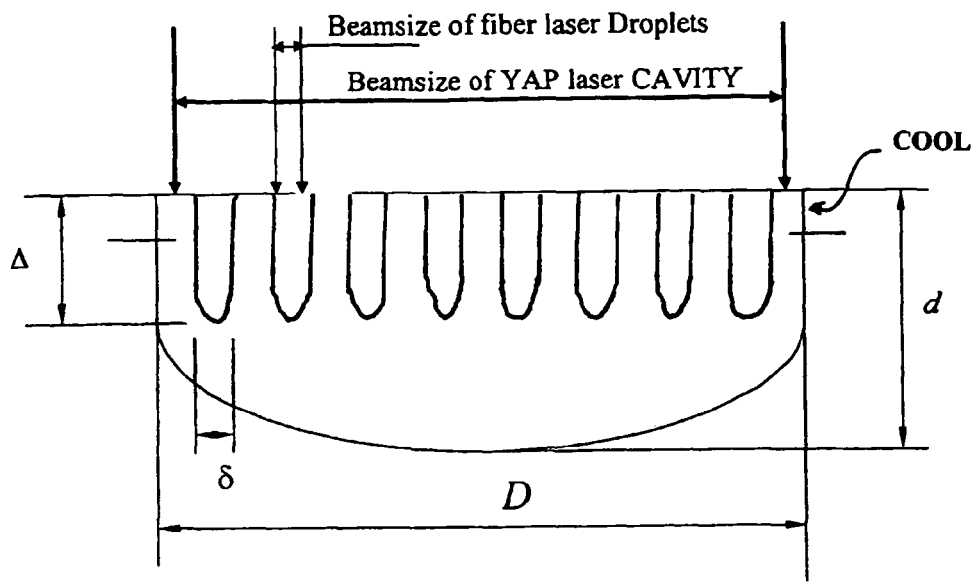
Figure 5B:
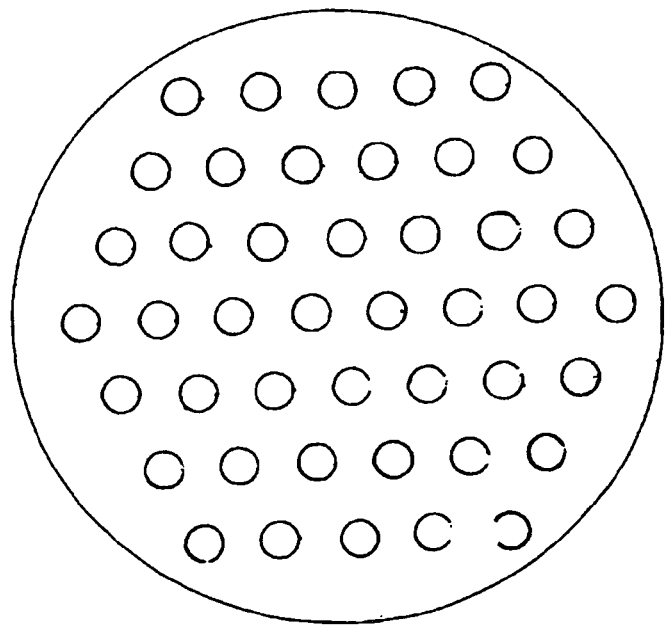

Many other crossing beam patterns are possible using the teachings of this invention to form energy droplets under the skin. Some of these are suggested in FIGS. 5A through 5I. FIGS. 5A and 5B show a pattern created by 44 short pulse narrow beams directed into a large energy cavity. Preferably the surface of the skin is cooled so that 44 energy droplets are created in tiny regions about 1 to 3 millimeters below the skin surface.

FIG. 5C shows a technique similar to the one shown in 5A and B, but here the energy cavity is created by a laser beam directed at an angle to assure that most of the energy droplets are created below the skin surface.

FIGS. 5D and 5E demonstrate a technique for using a beam splitter to permit the cavity creating beam and the energy droplet beam to be co-aligned.

FIGS. 5F and 5G is a similar technique where the two beans are angularly offset.

Figures 5H, 5I:
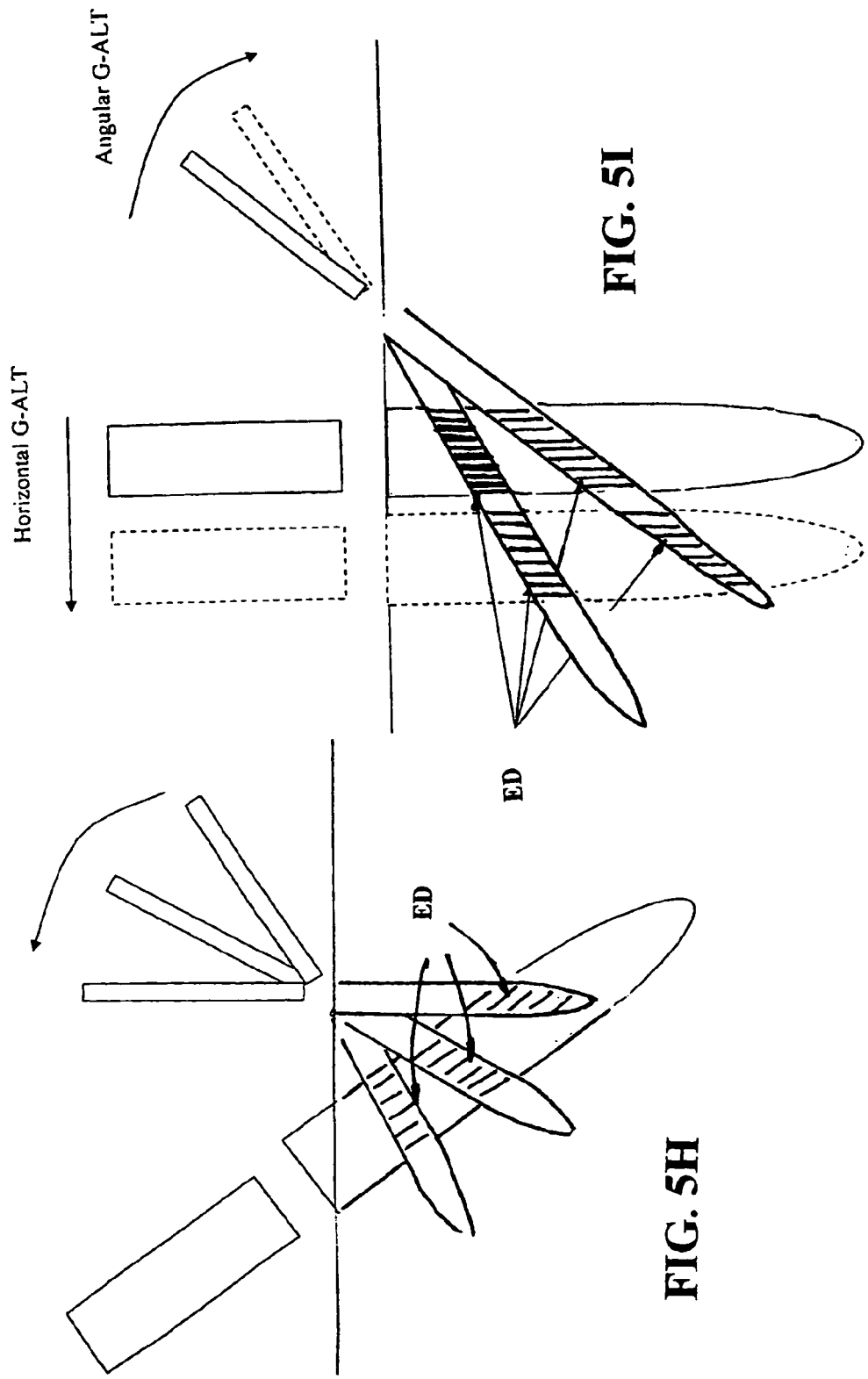

FIGS. 5H and 5I show techniques where one thermal cavity laser beam and one energy droplet beam are adjusted to create multiple energy droplets below the skin surface.

Other Applications of the Present Invention

The above embodiments describe techniques for skin treatments based on the concept that by utilizing thermal cavities and energy droplets to intentionally cause damage to tiny volumes of skin below the surface of the skin, natural skin renewal processes will be initiated in the skin that will extend beyond the region damaged to produce rejuvenated skin. This concept can be extended to other types of treatments. Some of these other types of treatments are discussed below:

Large Area Skin Rejuvenation

For large area skin rejuvenation a combination of 980 nm and 1440 nm is recommended. The 980 nm beam is to form energy cavity with deep penetration (up to 5 mm) and the 1440 nm beam or beams is to form energy drops with penetrations of about 0.33 mm. Short laser pulses of the energy droplets produce mechanical; removal of upper layers of skin and results in skin shrinkage and tightening. This combination is for large area skin rejuvenation including neo-collagen formation, sebaceous gland and bulge area stem cell mobilization.

Laser Assisted Anti-Aging Process for Skin

The first laser beam is made by YAP:Nd laser with deep penetration depth. This beam is used to heat up the large volume of tissue underneath the surface. The second beam is made by 1930 nm laser diode pulses, these short laser pulses are used to perforate the stratum corneum. Then an active topical agent (cream, gel, suspension, solution, etc) is applied. The active ingredient of the topical agents penetrates into the skin via micro openings and get into preheated tissue. Due to elevated temperature of the tissue the absorption and activity of the active ingredient increases and enhance the overall efficiency of the skin anti-aging procedure.

Treatment of Acne Scar Tissue

Applicants recommend 980 nm and 1930 nm for acne scar treatment. The 980 nm beam is to form the energy cavity with penetration several mm and the 1930 nm beam is to form energy drops with penetration is just 0.08 mm. The short laser pulses of 1930 um rupture the upper surfaces of a scar making the scar tissue more safer, and deeper pretending 980 um helps such surface rejuvenation. As above the skin surface should be cooled to prevent surface damage. This combination can also be used for skin rejuvenation.

Hair Removal

For a hair removal technique Applicants recommend a combination of 810 nm and 980 nm. The nm 980 nm beam is to form energy cavity and 810 nm beam is to form energy droplets. The 810 nm beam is for pigmented hair tissue, shaft and matrix, while the 980 nm beam is deeper penetration and less absorption in melanin for outside hair root channel tissue that contains blood vessels and stem cells. The 810 nm energy is strongly absorbed in the pigmented hair tissue and thus damages the hair tissue while at the same providing the thermal cavity. The purpose of the 980 nm energy droplets is to stimulate new skin tissue growth in the treated region of the skin. This combination is also good for skin rejuvenation. Another efficient combination for hair removal is a long pulse laser beam of 980 nm laser diode or 1079/1064 nm solid state Nd-laser as a thermal cavity and short Q-switched pulse of 1064 nm Nd:YAG laser as the energy droplets. The first laser beam creates thermal cavity and help to destroy stem cell enabling hair growth due to slow process of tissue coagulation and the second laser beam is absorbed by the pigment in the hair and ruptures the hair by high pressure induced by this second laser beam.

Treatment of Rhytides and Acne and Acne Scar Tissue

Applicants recommend a combination of 457 nm, 980 nm and 1440 nm for treatment of rhytides and acne and acne scar tissue. The 980 nm beam is to form energy cavity and the 1440 nm and 457 nm beams are to form multiple color energy drops.

Treatment of Telangiatesia and Pigmented Lesions

Applicants recommend 980 nm and 532 nm or 540 nm for telangiatesia and pigmented lesions treatments. The 980 nm is to form energy cavity and 532 nm or 540 nm is to form energy droplets. Wavelengths in the range of 980 nm provide uniform preheating of and around the vessels and blood plasma forming the energy cavity. The small blood vessels are then destroyed by the energy droplets of extremely short pulses of 532 nm or 540 nm laser beams which are strongly absorbed as shown in FIGS. 7 and 8.

Pigmented Lesions and Wrinkles

For treatment of pigmented lesions and wrinkles Applicants recommend a combination of 980 nm, 532 nm and 1440. The 980 nm beam is to form energy cavity with deep penetration (several mm) and 532 nm and/or 1440 nm are to form energy drops to treat pigmented lesions and wrinkles at the same time as described above.

Collagen Modification

For collagen modification 1440 nm beams be used for both the thermal cavity and the energy droplets. For the thermal cavity use a wide beam and long pulse and for the energy droplets use multiple narrow beams and of short pulses. These combinations can also be used for skin rejuvenation. Application is enhanced collagen modification for skin rejuvenation.

Laser Suppliers

All of the above combinations of wavelengths can be obtained by using powerful laser diodes. The laser diodes can be obtained from a number manufacturers like nLight, with offices in Vancouver, Canada; Coherent, with offices in Santa Clara, Calif. and IPG Photonics, with offices in Oxford, Mass.

Other laser suppliers include Palomar (Burlington, Mass.), Cynosure (Westford, Mass.), Candela (Wayland, Mass.), Eleme (Merrimack, N.H.), Sciton (Palo Alto, Calif.), Lumenis (Santa Clara, Calif.), Cutera (Brisbane, Calif.).

Table II below summarizes some preferred wavelength ranges, laser pulse energy and pulse rate ranges for both the first laser source to produce the thermal cavity and the second laser source to produce energy drop. The value of laser energy is that measured before the light is absorbed in skin tissue. The amount of energy absorbed in the skin is same for all lasers and such to produce a temperature rise about 5° C. for the thermal cavity with the diameter of the thermal cavity D is 10 mm. The diameter of the energy drop d is 2 mm and average temperature rise is 10° C. If the energy E is too high to obtain from a laser system the spot size should be decreased. Laser Energy is proportional to laser spot size diameter squared ($E \sim D^2$, $E \sim d^2$).

TABLE II

| Preheat Laser Source | | | Modulated Energy Droplet Laser source | | |
|---|---|---|---|---|---|
| Wavelength, nm, nanometers | Laser Energy, Joules | Laser Pulse duration range, ms, milliseconds | Wavelength, nm nanometers | Laser Energy, mJ, milli Joules | Laser Pulse duration range, microseconds |
| 890 nm | 27 | 1-20 ms | 640 nm | 330 | 0.01-1 |
| 915 nm | 33 | 1-20 ms | 670 nm | 440 | 0.01-1 |
| 980 nm | 41 | 1-20 ms | 532-540 nm | 110 | 0.01-1 |
| 980 nm | 41 | 1-20 ms | 457 and 1440 nm | 44 and 66 | 0.01-1 |
| 980 nm | 41 | 1-20 ms | 1930 nm | 17 | 0.01-1 |
| 980 nm | 41 | 1-20 ms | 1290 nm | 880 | 0.01-1 |
| 1064 nm | 54 | 0.1-50 ms | 532 nm | 110 | 0.01-1 |
| 1064 nm | 54 | 0.1-50 ms | 1320 nm | 660 | 0.01-1 |
| 1064 nm | 54 | 0.1-50 ms | 1440 nm | 66 | 0.01-1 |
| 1064 nm | 54 | 0.1-50 ms | 1064 nm | 980 | 0.01-0.2 |
| 1079 nm | 82 | 0.1-50 ms | 1540 nm | 102 | 0.01-1 |
| 1440 nm | 0.82 | 1-20 ms | 1930 nm | 17 | 0.01-1 |
| 1440 nm | 0.82 | 1-20 ms | 1440 nm | 66 | 0.01-1 |

The reader should understand that the above specific embodiments of the present invention are merely examples and that many changes and modifications could be made without departing from the important concepts of the present invention. For example, many sources of radiation at different wavelengths that are scattered and absorbed in tissue and skin with specific configuration and time relationship may be substituted for the lasers described in detail. In fact the above-described source of radiation could be any source of electromagnetic energy that meets the above-described criteria, such as microwave, radio frequency, light (laser diodes, light emitting diodes (LED), non-coherent light source), etc. Those sources of radiation could be combined to produce at least two wavelengths to form thermal cavity and energy drops with two significantly different pulse durations to produce modulated action. Therefore, the reader should determine to scope of the present invention by the appended claims and their legal equivalents.

We claim:

1. A laser skin treatment process, comprising the steps of:
   A) cooling a surface region of the skin to produce a cooled skin surface region,
   B) illuminating at least a portion of the cooled skin surface region, for a first time period of 900 microseconds with at least one preheat laser beam with sufficient optical energy to heat a first skin region below the cooled skin surface region to a first temperature-time profile that is close to but below a temperature-time profile that would cause tissue damage, said first region so heated with said first temperature-time profile defining a thermal cavity; and
   C) illuminating a sub-region of skin within said thermal cavity for a second time period of 0.2 microsecond with a plurality of laser beams, all of which are directed at the same time to the same sub-region of skin and adapted to apply a sufficient quantity of additional optical energy to said sub-region of skin to produce mechanical damage via ablation or disruption to skin tissue within the sub-region with no significant damage outside the sub-region, said additional quantity of optical energy in said sub-region defining an energy droplet;
   wherein said tissue damage in said sub-region stimulates a healing process that subsequently extends beyond the region damaged to produce rejuvenated skin tissue.

2. The laser skin treatment process as in claim 1 wherein said plurality of laser beams is provided by single laser beam that is separated into a plurality of laser beams, all directed to the sub-region of skin.

3. The laser skin treatment process as in claim 2 wherein said plurality of energy droplet laser beams is six energy droplet laser beams.

4. The laser skin treatment process as in claim 3 wherein said preheat laser beam is a laser beam with a peak wavelength chosen from the following group of wavelengths: 750 nm to 1450 nm, 1500 nm to 1850 nm, 2200 nm to 2300 nm; and said energy droplet laser beam is a laser beam with a peak wavelength chosen from the following group of wavelengths: 200 nm to 750 nm, 1400 nm to 1600 nm, 1850 nm to 3000 nm.

5. The laser skin treatment process as in claim 4 wherein said at least one preheat laser beam and said at least one energy droplet laser beam in terms wavelength, laser energy and pulse duration are provided respectively by laser sources listed in the following table:

| Preheat Laser Source | | | Modulated Energy Droplet Laser source | | |
|---|---|---|---|---|---|
| Wavelength, nm, nanometers | Laser Energy, Joules | Laser Pulse duration range, ms, milliseconds | Wavelength, nm nanometers | Laser Energy, mJ, milli Joules | Laser Pulse duration range, microseconds |
| 890 nm | 27 | 1-20 ms | 640 nm | 330 | 0.01-0.2 |
| 915 nm | 33 | 1-20 ms | 670 nm | 440 | 0.01-0.2 |
| 980 nm | 41 | 1-20 ms | 532-540 nm | 110 | 0.01-0.2 |
| 980 nm | 41 | 1-20 ms | 457 and 1440 nm | 44 and 66 | 0.01-0.2 |
| 980 nm | 41 | 1-20 ms | 1930 nm | 17 | 0.01-0.2 |
| 980 nm | 41 | 1-20 ms | 1290 nm | 880 | 0.01-0.2 |
| 1064 nm | 54 | 0.9-50 ms | 532 nm | 110 | 0.01-0.2 |
| 1064 nm | 54 | 0.9-50 ms | 1320 nm | 660 | 0.01-0.2 |
| 1064 nm | 54 | 0.9-50 ms | 1440 nm | 66 | 0.01-0.2 |
| 1064 nm | 54 | 0.9-50 ms | 1064 nm | 980 | 0.01-0.2 |
| 1079 nm | 82 | 0.9-50 ms | 1540 nm | 102 | 0.01-0.2 |
| 1440 nm | 0.82 | 1-20 ms | 1930 nm | 17 | 0.01-0.2 |
| 1440 nm | 0.82 | 1-20 ms | 1440 nm | 66 | 0.01-0.2. |

6. The laser skin treatment process as in claim 4 wherein the energy droplet laser beam is a laser beam having a peak wavelength of about 1079 nm and the preheat laser beam is a laser beam having a peak wavelength of about 1560 nm.

7. The laser skin treatment process as in claim 4 where said skin surface is cooled with cold air.

8. The laser skin treatment process as in claim 4 wherein said at least one preheat laser beam and said at least one energy droplet laser beam are applied via a laser hand piece.

9. The laser skin treatment process as in claim 1 wherein at least one preheat laser beam and said at least one energy droplet laser beam are delivered via optical fibers.

10. The laser skin treatment process as in claim 9 wherein said laser hand piece is pre-cooled and said skin surface is cooled through physical contact with the laser hand piece.

11. The laser skin treatment process as in claim 1 wherein said process is adapted to treat a condition chosen from the following group of skin conditions:

D) acne scaring

E) other scaring

F) unwanted hair

G) rhytides

H) telangiatesia

I) wrinkles

J) skin ulcers.

* * * * *